United States Patent
Leturcq (12)

(10) Patent No.: US 6,790,662 B1
(45) Date of Patent: Sep. 14, 2004

(54) METHOD OF ISOLATING CD8+ CELLS, AND RELATED HYBRIDOMA CELLS ANTIBODIES AND POLYPEPTIDES

(75) Inventor: Didier Leturcq, San Diego, CA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/521,527

(22) Filed: Mar. 8, 2000

Related U.S. Application Data

(60) Provisional application No. 60/124,253, filed on Mar. 12, 1999.

(51) Int. Cl.[7] .................................................. C12N 5/06
(52) U.S. Cl. ........................ 435/343.2; 435/7.2; 435/30; 435/325; 435/332; 435/346; 435/372; 436/501; 436/548; 530/350; 530/388.2; 530/388.75
(58) Field of Search .......................... 435/7.2, 30, 325, 435/332, 346, 372, 343.2; 436/501, 548; 530/350, 388.2, 388.75

(56) References Cited

U.S. PATENT DOCUMENTS 5,645,837 A * 7/1997 Jameson et al. ......... 424/185.1
6,001,962 A    12/1999 Ramer et al.

FOREIGN PATENT DOCUMENTS

| EP | 0 699 907 A2 | 3/1996 |
|---|---|---|
| WO | WO95/34817 | 12/1995 |
| WO | WO 99/54345 A1 | 10/1999 |

OTHER PUBLICATIONS

VanderVegt, FP et al. J. Exp. Med. 177:1587–1592.*
Whiteside, TL et al. Blood. 81(8):2085–2092.*
Nabholz M. and H.R. Macdonald (1983) Annual Review of Immunology 1:273–306.
Riddell S.R. and P.D. Greenberg (1994) Current Topics in Microbiology and Immunology 189:9–34.
Riddell, S. R. and P. D. Greenberg (1995) Annual Review of Immunology 13:545–586.
Horgan K. and S. Shaw (1994) Current Protocols in Immunology 2:7.4.1.
Lea, T. et al., (1988) Journal of Molecular Recognition 1(1):9–18.
Kanof M.E. (1994) Current Protocols in Immunology 2:7.1.1.
Knaof M.E. (1994) Current Protocols in Immunology 2:7:3:1.
Eichmann et al., "Affinity Enhancement and Transmembrane Signaling Are Associated with Distinct Epitopes on the CD8 aμ Heterodimer", The Journal of Immunology, vol. 147, No. 7, pp 2075–2081 (Oct. 1991).
Littman et al., "The Isolation and Sequence of the Gene Encoding TB: A Molecule Defining Functional Classes of T Lymphocytes", Cell, vol. 40, No. 2, pp 237–246 (1985), GenPept Accession P01732, Version P01732 GI: 116035.
Litessier et al., "enrichment in Tumor–Reactive CD8+ T–Lymphocytes by Positive Selection from the Blood and Lymph Nodes of Patients with Head and Neck Cancer", Cancer Research, vol. 51, pp 3891–3899 (Aug. 1991).
Prince et al., "Preparation of CD8 bright and CD8 dim Lymphocyte Populations Using Two Positive Selection Methods in Tandem", The Journal of Immunological Methods, vol. 165, pp 139–148 (1993).
Stanciu et al., "Production of IL–8 and IL–4 By Positively and Negatively Selected CD4+ and CD8+ Human T Cells Following a Four–Step Cell Separation Method Including Magnetic Cell Sorting (MACA)", The Journal of Immunological Methods, vol. 189, pp 107–115 (1996).

\* cited by examiner

*Primary Examiner*—G. R. Ewoldt

(57) ABSTRACT

This invention provides a method of isolating CD8+ cells which employs an antibody which specifically binds to CD8 molecules present on the surface of CD8+ cells but does not activate the CD8+ cells once bound. This invention also provides related hybridoma cell lines, monoclonal antibodies, antigenic polypeptides, isolated CD8+ cells, and kits.

5 Claims, No Drawings

METHOD OF ISOLATING CD8+ CELLS, AND RELATED HYBRIDOMA CELLS ANTIBODIES AND POLYPEPTIDES

This application claims priority from U.S. provisional patent application 60/124,253 filed Mar. 12, 1999 and entitled "Method if isolating CD8+ cells and related hybridoma cells, antibodies and polypeptides."

Throughout this application, various publications are cited. The disclosure of these publications is hereby incorporated by reference into this application to describe more fully the state of the art to which this invention pertains.

FIELD OF THE INVENTION

This invention relates to a positive selection method for isolating $CD8^+$ cells using certain CDB-specific antibodies. The isolated $CD8^+$ cells have importance as vehicles for combating viral infections and tumors.

BACKGROUND OF THE INVENTION

In humans, $CD8^+$ cells play a vital role in the immune system's ability to defend against potentially harmful foreign entities, such as bacteria and viruses [1]. $CD8^+$ cells circulate in the blood and possess on their surface the CD8 protein. When necessary, these cells are converted into cytotoxic cells (i.e. cell-killing cells) which proceed to destroy foreign cells, viruses, and other harmful pathogens present in the subject [2]. Because of $CD8^+$ cells' effective role in host defense, they hold great potential in isolated form as therapeutics for treating disorders such as viral infections and malignancies [3].

In the past, purification of human $CD8^+$ cells has been achieved by negative selection. Specifically, peripheral blood mononuclear cells ("PBMC's") are incubated with a cocktail of monoclonal antibodies specific for non-CDS sub-populations. These sub-populations include, for example, B-cells, $CD4^+$ cells, NK cells, macrophages and neutrophils, and each contains specific, non-CD8 "markers". The sub-populations are then removed from the resulting antibody cocktail using magnetic beads [4]. This technique has certain major disadvantages. The first is that several monoclonal antibodies are required for removing non-$CD8^+$ cells. The second is that the resulting $CD8^+$ population suffers from contamination from non-$CD8^+$ cells that possess relatively low levels of non-CD8 markers. Finally, when a magnetic separation procedure is used to remove all non-$CD8^+$ cells, a large number of magnetic beads are needed.

SUMMARY OF THE INVENTION

This invention provides a method of isolating $CD8^+$ cells which comprises the steps of (a) contacting a sample of isolated peripheral mononuclear blood cells with a first antibody which specificall bind to the sequence AAEGLDTQRFSG, (SEQ ID NO:1) or portion thereof, on CD8 molecules present on the surface of $CD8^+$ cells but does not activate the $CD8^+$ cells once bound thereto, under conditions permitting the formation of a first complex between the $CD8^+$ cell and first antibody;

(b) separating from the sample any first antibody not present in the resulting first complex;

(c) contacting the sample with a second, immobilized antibody which specifically binds to the first antibody in the first complex, under conditions permitting the formation of an immobilized, second complex between the first complex and the second antibody, thereby immobilizing the $CD8^+$ cells present in the sample;

(d) separating from the resulting immobilized second complex the cells present in the sample which were not immobilized in step (c);

(e) contacting the immobilized second complex under suitable conditions with an agent which causes the dissociation of the second complex into $CD8^+$ cells and an immobilized third complex between the first antibody and second antibody; and (f) separating the immobilized third complex from the $CD8^{S+}$ cells, thereby isolating the $CD8^+$ cells.

This invention also provides a hybridoma cell line which produces a monoclonal antibody which specifically binds to CD8 molecules present on the surface of $CD8^+$ cells but does not activate the $CD8^+$ cells. This invention further provides monoclonal antibodies produced by each of the instant hybridoma cell lines. Finally, this invention provides related polypeptides, isolated $CD8^+$ cells and kits.

DETAILED DESCRIPTION OF THE INVENTION

The hybridoma cell lines designated 37B1 and 8G6 were deposited on Dec. 11, 1997 and Mar. 4, 1999 respectively, pursuant to, and in satisfaction of, the requirements of the Budapest Treaty on the International Recognition of the Deposit of Microorganisms for the Purposes of Patent Procedure with the American Type Culture Collection (ATCC), 10801 University Boulevard, Manassas, Va. 20010-220009 under ATCC Accession Nos. HB-12441 and HB-12657, respectively.

This invention provides a method of isolating $CD8^+$ cells by employing an anti-CD8 antibody, along with certain other reagents. Specifically, this invention provides a method of isolating $CD8^+$ cells which comprises the steps of (a) contacting a sample of isolated peripheral mononuclear blood cells with a first antibody which specifically binds to the sequence AAEGLDTQRFSG, (SEQ ID NO:1) or portion thereof, on $CD8^+$ molecules present on the surface of $CD8^+$ cells but does not activate the $CD8^+$ cells once bound thereto, under conditions permitting the formation of a first complex between the $CD8^+$ cell and first antibody;

(b) separating from the sample any first antibody not present in the resulting first complex;

(c) contacting the sample with a second, immobilized antibody which specifically binds to the first antibody in the first complex, under conditions permitting the formation of an immobilized, second complex between the first complex and the second antibody, thereby immobilizing the $CD8^+$ cells present in the sample;

(d) separating from the resulting immobilized second complex the cells present in the sample which were not immobilized in step (c);

(e) contacting the immobilized second complex under suitable conditions with an agent which causes the dissociation of the second complex into $CD8^+$ cells and an immobilized third complex between the first antibody and second antibody; and (f) separating the immobilized third complex from the $CD8^+$ cells, thereby isolating the $CD8^+$ cells.

As used herein, a "$CD8^+$ cell" means a T-cell having on its surface the CD8 protein. In the preferred embodiment, the $CD8^+$ cells are human $CD8^+$ cells. The $CD8^+$ cells can be from any CD8+ cell-possessing species. "Isolating" CD8+ cells means obtaining a population of peripheral mononuclear blood cells wherein the ratio of CD8+ cells to non-CD8+ cells is at least about 7:1. In the preferred embodiment of this invention, this ratio is at least about 9:1.

This invention employs several types of antibodies which specifically bind to given epitopes. More particularly, this invention uses a "first antibody" which specifically binds to the sequence AAEGLDTQRFSG (SEQ ID NO:1), or portion thereof, on CD8 molecules present on the surface of CD8+ cells but does not activate the CD8+ cells once bound thereto. Here, CD8+ cell "activation" means causing CD8+ cells to express Y-interferon ("Y-IFN"). This activation can be measured using routine methods such as sandwich ELISA assays, which can be performed using commercially available kits.

Such first antibodies include, but are not limited to, the monoclonal antibodies produced by the hybridoma cell lines 37B1 (ATCC Accession No. HB-12441) and 8G6 (ATCC Accession No. HB-12657). Conditions which permit these antibodies to bind to but not activate CD8+ cells are well known in the art. These conditions include, for example, a suitable buffer such as Ca2+ and Mg2++-free Dulbecco's Phosphate Buffer Saline (DPBS) containing 1% Human serum Albumin (HAS) and 0.2% sodium citrate and gentle mixing by "end over end" rotation on a rotator set at 4 rpm.

As used herein, the term "antibody" includes, but is not limited to, both naturally occurring and non-naturally occurring antibodies. Specifically, the term "antibody" includes polyclonal and monoclonal antibodies, and binding fragments thereof. Furthermore, the term "antibody" includes chimeric antibodies and wholly synthetic antibodies, and fragments thereof. In one embodiment, the antibody is a a monoclonal antibody. The monoclonal antibody can be human, or that of another species including, for example, mouse and rabbit. In this invention, an antibody which "specifically" binds to a stated epitope binds to that epitope with a dissociation constant of at least about 10-fold less than the dissociation constant with which it binds to any other epitope. In one embodiment, this dissociation constant ratio is at least about 100. In the preferred embodiment, this dissociation constant ratio is at least about $10^3$.

The "second antibody" used in the instant method can be any antibody which specifically recognizes an epitope on any portion of the first antibody. In the preferred embodiment, the second antibody specifically recognizes a portion of the constant (Fc) region of the first antibody. Such anti-Fc antibodies are commercially available and include, for example, sheep anti-mouse antibody immobilized on magnetic beads [5].

The agent that causes dissociation of the immobilized second complex into CD8+ cells and immobilized antibodies can be any agent which successfully competes with the CD8 molecule for specific binding to the first antibody. In the preferred embodiment, this agent is the polypeptide designated CD8-3 having the sequence AAEGLDTQRFSG (SEQ ID NO:1). In one embodiment, the immobilized second antibody comprises an antibody operably affixed to a magnetic bead.

This invention also provides a hybridoma cell line which produces a monoclonal antibody which specifically binds to CD8 molecules present on the surface of CD8+ cells but does not activate the CD8+ cells. In one embodiment, the hybridoma cell line is selected from the cell lines designated 37B1 (ATCC Accession No. HB-12441) and 8G6 (ATCC Accession No. HB-12657). This invention further provides the monoclonal antibodies produced by each of the instant hybridoma cell lines.

This invention further provides a polypeptide useful for generating the instant monoclonal antibody that comprises the amino acid sequence AAEGLDTQRFSG (SEQ ID NO:1). In the preferred embodiment, the polypeptide is the polypeptide designated CD8-3 and having the amino acid sequence AAEGLDTQRFS (SEQ ID NO:2). The instant polypeptide can optionally comprises one or more additional amino acid residues at the C-terminal or N-terminal end. In the preferred embodiment, the polypeptide has the sequence NKPKAAEGLDTQRFSGKRLG (SEQ ID NO:3).

This invention further provides a population of CD8+ cells isolated by the instant method.

Finally, this invention provides a kit for use in isolating CD8+ cells which comprises, in separate compartments, (a) an antibody which specifically binds to the sequence AAEGLDTQRFSG (SEQ ID NO:1) or portion thereof, on CD8 molecules present on the surface of CD8+ cells, but does not activate the CD8+ cells once bound thereto; and (b) an agent which causes the dissociation of a CD8+ cell-antibody complex. In one embodiment, the agent which causes the dissociation of a CD8+ cell-antibody complex comprises the polypeptide having the sequence AAEGLDTQRFSG (SEQ ID NO:1). In the preferred embodiment, the agent is the polypeptide consisting of the sequence AAEGLDTQRFSG (SEQ ID NO:1).

The instant kit can further comprise reagents useful for performing the binding and dissociation steps of the instant method. The components of the instant kit can either be obtained commercially or made according to well known methods in the art. In addition, the components of the instant kit can be in solution or lyophilized as appropriate. In the preferred embodiment, the kit further comprises instructions for use.

The following procedures relating to the instant invention are routine in the art: isolating peripheral mononuclear blood cells from which the CD8+ cells are in turn isolated [6]; separating unbound antibodies and cells from a sample containing bound antibodies and/or cells via centrifugation or spinning membrane; and immobilizing antibodies via polystyrene flasks, columns or beads [4,7].

This invention will be better understood by reference to the Experimental Details which follow, but those skilled in the art will readily appreciate that the specific experiments detailed are only illustrative of the invention as described more fully in the claims which follow thereafter.

Experimental Details

Rationale

Human CD8+ cells can be isolated from preparations of peripheral blood mononuclear cells (PBMC's) by either positive or negative selection. Positive selection results in a highly-purified population of CD8+ cells. Negative selection, while resulting in sufficient numbers of CD8+ cells, has low levels of contaminating non-CD8 populations remaining after the selection procedure.

The idea was to generate an antibody which has high affinity for CD8+ cells, does not activate the cells during the selection process, and is capable of being easily eluted from the cells. An anti-peptide antibody appeared to meet these criteria. However, it was known that anti-peptide antibodies might be of low affinity and may recognize the linear peptide sequence exclusively, preventing reactivity with native antigen.

It was necessary that the anti-CD8 antibody not activate the cells during the selection process, as it would lessen their ability to effectively act as naive responder cells during in vitro stimulation protocols. The use of peptide release to selectively isolate a cell population has been show by Tseng-Law, et al. [8] for CD34+ cells.

Methods

The CD8 alpha chain was examined for hydrophilic sequences and four peptides selected. All were coupled to keyhole limpet hemocyanin (KLH) as carrier and used to immunize mice. A C-terminal amino acid was added to each of the peptides coupled to KLH to make the monoclonal antibodies. Antisera from the mice were evaluated for the ability to recognize both peptide and native CD8 on the surface of T cells. Only one of the four peptides was capable of recognition of both antigenic forms of CD8. Monoclonal antibodies were generated to this peptide and the resulting antibody used to isolate CD8+ cells from a PBMC preparation. The antibody was successful in isolating a population of highly-purified CD8+ cells (Table 1) which were not activated by the isolation procedure (Table 2).

TABLE 1

Purification of CD8+ Cells by Positive Selection Analyzed by Flow Cytometry*

| CELL TYPE | PBMC % Fluorescence (Range) | POST SELECTION % Fluorescence (Range) |
|---|---|---|
| CD8 T cells | 15 (7–24) | 82 (56–95) |
| CD4 T cells | 36 (14–52) | 2 (0.1–10) |
| CD14 Monocytes | 15 (7–26) | 0.8 (0.2–2) |
| CD15 Neutrophils | 12 (8–21) | 0.6 (0.1–3) |
| CD19 B cells | 2 (0.4–7) | 3 (0.5–9) |
| CD56 NK cells | 6 (2–17) | 6 (0.1–20) |

*Summary of 10 normal donors

TABLE 2

Activation of CD8+ Cells Isolated By Negative or Positive Selection (Assessed by IFNγ Production)

| Cells | Negative Selection (pg/ml) | Positive Selection (pg/ml) |
|---|---|---|
| un-stimulated | 20 | 20 |
| allo-stimulation | 1440 | 3600 |

References

1. Nabholz M. and H. R. MacDonald (1983) Annual Review of Immunology 1:273–306.
2. Riddell S. R. and P. D. Greenberg (1994) Current Topics in Microbiology and Immunology 189:9–34.
3. Riddell S. R. and P. D. Greenberg (1995) Annual Review of Immunology 13:545–586.
4. Horgan K and S. Shaw (1994) Current Protocols in Immunology 2:7.4.1.
5. Lea T, et al. (1988) Journal of Molecular Recognition 1(1):9–18.
6. Kanof, M. E., et al. (1994) Current Protocols in Immunology 2:7.1.1.
7. Kanof M. E. (1994) Current Protocols in Immunology 2:7:3:1.
8. PCT International Publication No. WO 95/34817.

---

What is claimed is:

1. A method of isolating human CD8+ cells which comprises the steps of:
   (a) contacting a sample of isolated peripheral mononuclear blood cells with a first antibody which specifically binds to an epitope comprising AAEGLDTQRFSG (SEQ ID NO:1), on CD8 molecules present on the surface of human CD8+ cells but does not activate the CD8+ cells once bound thereto, under conditions permitting the formation of a first complex between the CD8+ cell and the first antibody;
   (b) separating from the sample any first antibody not present in the first complex;
   (c) contacting the sample with an immobilized second antibody which specifically binds to the first antibody in the first complex, under conditions permitting the formation of an immobilized second complex between the first complex and the second antibody, thereby immobilizing the CD8+ cells present in the sample;
   (d) separating the immobilized second complex from the sample;
   (e) contacting the immobilized second complex with an agent, which under suitable conditions causes dissociation of the second complex into CD8+ cells and an immobilized third complex between the first antibody and second antibody; and
   (f) separating the immobilized third complex from the CD8+ cells, thereby isolating the CD8+ cells.

2. The method of claim 1, wherein the first antibody is a monoclonal antibody.

3. The method of claim 2, wherein the monoclonal antibody is produced by a hybridoma cell line selected from the group consisting of the cell line designated 37B1 (ATCC Accession No. HB-12441) and the cell line designated 8G6 (ATCC Accession No. HB-12657).

4. The method of claim 1, wherein the immobilized second antibody comprises an antibody operably affixed to a magnetic bead.

5. The method of claim 1, wherein the agent which causes the dissociation of immobilized third complex is the polypeptide designated CD8-3 having the amino acid sequence AAEGLDTQRFSG (SEQ ID NO:1).

* * * * *

SEQUENCE LISTING

<160> NUMBER OF SEQ ID NOS: 3

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence:synthetic
      peptide corresponding to CD8+ epitope

<400> SEQUENCE: 1

Ala Ala Glu Gly Leu Asp Thr Gln Arg Phe Ser Gly
 1               5                  10

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 2

Ala Ala Glu Gly Leu Asp Thr Gln Arg Phe Ser
 1               5                  10

<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence: synthetic

```
                                    -continued peptide

<400> SEQUENCE: 3

Asn Lys Pro Lys Ala Ala Glu Gly Leu Asp Thr Gln Arg Phe Ser Gly
  1               5                  10                  15

Lys Arg Leu Gly
            20
```